United States Patent [19]

Eberling et al.

[11] Patent Number: 4,524,319

[45] Date of Patent: Jun. 18, 1985

[54] METHOD FOR THE DETERMINATION OF KINETICS OF STRUCTURE FORMATION IN A BINDER

[75] Inventors: Igor L. Eberling; Lev A. Tereschenko; Nikolai I. Nikolaev; Arian M. Yakovlev; Vitaly I. Kovalenko, all of Leningrad; Nikolai K. Lipatov, Apatity Murmanskoi; Ruben A. Tatevosian; Mikhail Y. Titov, both of Moscow, all of U.S.S.R.

[73] Assignee: Territorialnoe Geolgicheskoe Upravlenie Tsentralnykh Raionov, Moscow, U.S.S.R.

[21] Appl. No.: 352,516

[22] Filed: Feb. 26, 1982

[30] Foreign Application Priority Data

Apr. 27, 1981 [SU] U.S.S.R. ............... 3270005

[51] Int. Cl.³ .............. G01R 27/02; G01N 11/00
[52] U.S. Cl. .................... 324/65 R; 73/53
[58] Field of Search ............. 73/53, 432 R, 432 Z; 324/65 P, 65 R, 61 R, DIG. 1; 374/53

[56] References Cited

U.S. PATENT DOCUMENTS 3,243,702  3/1966  Schuck .............. 324/DIG. 1
4,120,166  10/1978 Brooks .............. 324/65 P X
4,178,544  12/1979 Hoffman ............. 324/65 P X

FOREIGN PATENT DOCUMENTS 280962  12/1970  U.S.S.R. .
511548   9/1976  U.S.S.R. ............... 73/432 Z

OTHER PUBLICATIONS

Rakhimov: "Investigation of Cohesion Forces between Cement Stone and Rocks"–Saigims–Issue 6–1972, Tashkent–USSR.

Primary Examiner—Stanley T. Krawczewicz
Assistant Examiner—Jose M. Solis
Attorney, Agent, or Firm—Burgess, Ryan & Wayne

[57] ABSTRACT

A method for monitoring structural changes in a binder in contact with a solid object, while the binder is curing. Conductivity measuring pick-ups are placed in the binder mass and at the boundary between the binder and the solid object. A low amplitude AC voltage is applied to each pick-up at a low frequency, and the pick-up output signals are compared by a differential inductive bridge. The difference between the output signals is indicative of the extent of adhesion of the binder to the solid object. Preferably, only those components of the pick-up signals which are in phase with the applied AC voltage are employed for the comparison.

2 Claims, 6 Drawing Figures

METHOD FOR THE DETERMINATION OF KINETICS OF STRUCTURE FORMATION IN A BINDER

The invention relates to the field of investigations of binders, and more specifically it deals with method and apparatus for the determination of kinetics of structure formation in binders.

The method according to the invention may be advantageously used for the investigations of kinetics of structure formation and adhesive properties of quick-setting mixes of binders.

The method and apparatus to the invention may be used for specification and certification of binders in their mass-scale production.

The method and apparatus according to the invention may also find application in evaluating ageing and metamorphism of binders during storage.

The method and apparatus according to the invention may be most preferably used in conducting plugging operations under complicated conditions during well-drilling.

Methods for the investigation of kinetics of structure formation are widely known which are applicable to binders featuring comparatively long setting times. These methods involve recording discrete characteristics during hardening by way of destruction of a starting material.

These methods do not make it possible to obtain complete and reliable information on the kinetics of the process of structure formation in the investigation of kinetics of structure formation in quick-setting binders.

In view of an ever growing demand in the use of quick-setting mixes of binders, there is a long felt need in the investigation and determination of kinetics of structure formation in binders and in measurement of their adhesive characteristics.

There are widely known methods for measuring adhesion involving breaking-off a sample of a binder from the surface of a solid body (cf. "Some Problems of the Construction of Wells under Complicated Conditions in Uzbekstan (in Russian), Issue 6, SAIGIMS, Tashkent, 1972; A. I. RAkhimov "Investigation of Forces of Cohesion between Cement Stone and Rocks", pp. 137, 138).

These methods may be used for the investigation of the adhesion only using individual samples (that is at discrete points) so that a continuous picture of variation of the adhesion during structure formation and hardening of cement stone cannot be obtained.

Obtaining continuous adhesion characteristics is especially important in using quick-setting binders for liquidation of troublesome zones during drilling and plugging operations.

Known in the art is an apparatus enabling the determination of kinetics of structure formation in binders, comprising an a-c voltage generator connected by means of a coupling device to a cell and to a recording instrument. The coupling device comprises a solenoid imparting oscillations to the cell containing a sample of a binder and suspended by means of strings, and in inductive receiver for receiving oscillations of the cell. The recording instrument comprises an oscillograph recording the amplitude of oscillations of the cell, the changes in the amplitude being used for the determination of the resonance frequency of the cell containing the sample of a binder. This frequency characterizes the kinetics of structure formation (cf. USSR Inventor's Certificate No. 280962). This prior art apparatus does not make it possible to obtain a continuous picture of changes in the structure because at least 40–50 seconds are needed to record each value of the resonance frequency so that the apparatus cannot be used for the determination of kinetics of structure formation in quick-setting mixes of binders. The error of the apparatus strongly depends on external factors (vibrations, pressure, temperature, and the like), and it also hampers the evaluation of the influence of such factors on the structure formation.

It is an object of the invention to provide a method and apparatus for the determination of kinetics of structure formation in quick-setting binders during formation of structure of an artificial stone.

With this object in view, there is provided a method for the determination of kinetics of structure formation in binders, comprising subjecting a product made of a binder to an external action and recording its response to this action, wherein according to the invention, for the purpose of subjecting the product to an external action, a voltage is applied to the product, and the electrical conductivity of the product is measured during its structure formation.

The electrical conductivity is preferably measured in two zones of the product made of a binder, one zone being located within the volume of the product and the other at the boundary with a solid body, the value of adhesion to the solid body being determined by the difference in the electrical conductivities of the two zones.

Measurement in two zones makes it possible to determine the adhesive properties of binders.

For carrying out the method for the determination of kinetics of structure formation, there is provided an apparatus comprising an a-c voltage generator which is connected by means of a coupling device to a product made of a binder for acting thereupon and to a device for recording the response of the product to this action, wherein, according to the invention, the coupling device comprises a pick-up for measuring the electrical conductivity which is installed in the product and connected to the a-c voltage generator and, via through a series circuit including a differential inductive bridge circuit, a voltage amplifier, and a phase detector to the device for recording the response of the product to the action by the generator.

The apparatus preferably comprises a second pick-up for measuring the electrical conductivity which is installed in the product made of a binder in the zone of its contact with the solid body and connected to the a-c voltage generator and to the input of the differential inductive bridge circuit.

The provision of two pick-ups makes it possible to determine the adhesive characteristics of binders.

The method and apparatus according to the invention make it possible to determine and investigate kinetics of processes of structure formation and adhesive characteristics of an artificial stone in the course of its hardening at all stages beginning with mixing of a binder up to the completion of the strength process both in individual samples and finished products without destruction to the latter. In addition, the method and apparatus according to the invention enable both manufacturing and delivery tests as well as certification of quick-setting binders during structure formation of an artificial stone. The method and apparatus according to the invention make it possible to control the process of structure formation in binders during plugging of wells during drilling directly within the well.

The invention will now be described in details with reference to specific embodiments illustrated in the accompanying drawings, in which.

During mixing and hardening, binders pass in a sequence through several stages of their state each being characterized by certain physico-mechanical characteristics. The structure of the binder changes accordingly as the transition from semi-fluid state to the state of a moulded artificial stone occurs. A certain value of electrical conductivity corresponds to each state since the transition from the ionic conductor (liquid) to the conductor in the form of a solid body takes place. After the hardening is completed, the majority of artificial stones become poor conductors or even insulators. By recording the nature of change in the electrical conductivity during the formation of an artificial stone one can follow the process of structure formation on the basis of such changes and distinguish in a sufficiently distinct manner the stages of formation of the artificial stone. Measurement of electrical conductivity requires insertion of electrodes in the body of the would be stone, and in accordance with the method for the determination of kinetics of structure formation of the invention, an a-c voltage is applied to such electrodes. The voltage frequency should be high enough so as to minimize the error due to the capacitance of a double layer which is formed around an electrode immersed in a slurry of a mixed binder during the measurement. At the same time, this frequency should be below the frequency of molecular and complexing processes occurring in the binder during formation of structure of an artificial stone. Frequencies within the range from 5 to 20-30 kHz comply with these requirements. As shown by experimental studies, a frequency of about 10 kHz is to be regarded as the most preferred frequency. A voltage applied to a sample or product by means of electrodes should not exceed the value of between 30 and 50 mV since otherwise interferences may occur caused by electrolysis, and the picture of changes in the electrical conductivity would be substantially distorted. Interference caused by double layer and processes of relaxation at the molecular and complexing levels may be substantially reduced in measuring only the active component of the electrical conductivity, which may be ensured in carrying out the method.

Figure 1:
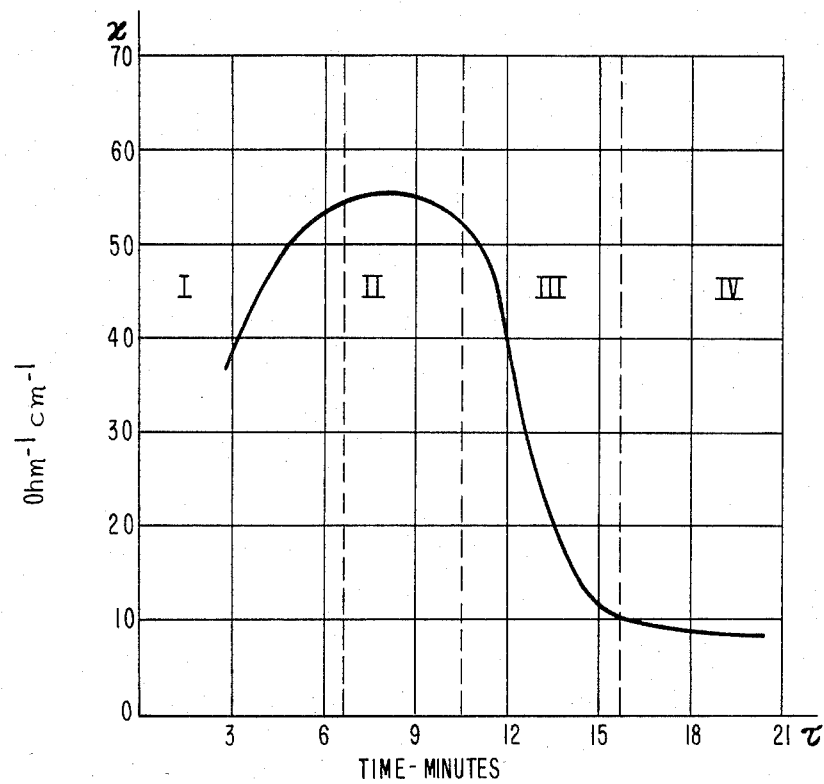
FIG. 1 shows a curve representing the kinetics of the process of structure formation in cement stone obtained by recording the relationship of the value of the electrical conductivity v. time during formation of the cement stone.

An example of the study of kinetics of structure formation in a quick-setting cement slurry is shown in FIG. 1. Time $\tau$ in minutes is plotted on the abscisse and the electrical conductivity $\varkappa_o$ in $Ohm^{-1} cm^{-1}$ is plotted on the ordinates.

The curve is bell-shaped, wherein the ascendant branch-stage I—is characteristic of the growth of the electrical conductivity during dissolution of the binder (hydration).

A point of an abrupt change in the steepness of the curve indicates the end of the stage I of hydration.

The flat character of the curve forming a plateau indicates to a material deceleration of the rate of growth of the electrical conductivity. The flat portion characterizes the stage II of the process of structure formation—the stage of coagulation. The descendant branch of the curve indicates to an abrupt drop of the electrical conductivity. The portion of the curve to the right of the flat portion up to the point of bend characteristics the condensation and crystallization stage of the process of structure formation—stage III.

After the bend point, the curve becomes flat and further the electrical conductivity decreases very slightly or remains unchanged. This is the last stage IV of the structure formation.

The following conclusions may be drawn from the point of view of the kinetics of structure formation processes of dissolution prevail at the stage I, which is shown by the growth of the electrical conductivity. The rate of hydration changes with the change in the degree of hydration. A three-dimensional frame of the coagulation structure is formed by the end of the first stage.

Stage II. A substantial deceleration of the growth of the electrical conductivity occurs. The development of the coagulation structure of the cement slurry prevails at the stage II.

Stage III. A three-dimentional frame of the condensation and crystallization structure is formed. Processes of structure formation occur in an intense manner. Coagulation contacts develop into crystallization contacts. The electrical conductivity drops abruptly which is due to a decrease in the concentration of unbonded ions participating in the formation of hydrate crystalline compounds.

Stage IV. Basic strength increase occurs.

Adhesion of binders to solid bodies is strongly associated with the process of structure formation at the interface binder—solid body. By measuring the value of the electrical conductivity one could monitor the process of structure formation, and by recording the difference in processes of structure formation at the boundary with a solid body and deep (within the volume of) in the binder, this difference may be used as the basis for assessing the adhesion of a binder being tested to the solid body. Therefore, the parallel recording of the process of the change in the electrical conductivity within the body of the binder and at the boundary thereof with a solid body, one can evaluate the adhesion of the binder to the solid body. For that purpose, an additional pair of electrodes should be placed at the boundary with the solid body, and the change in the electrical conductivity should be recorded similarly to the measurement of kinetics of structure formation.

Figure 2:
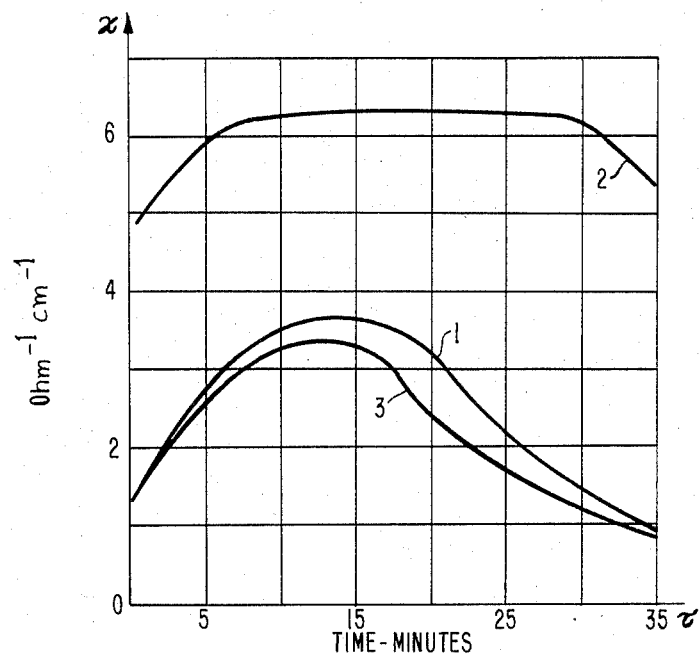
FIG. 2 shows curves of the electrical conductivity representing the relationship of electrical conductivity v. time of formation of structure of cement stone within the body of the stone and in the zone of contact with listvenite and sandstone.

FIG. 2 shows three curves representing a change in the electrical conductivity during formation of a cement stone in contact with listvenite and sandstone, the curve 1 showing the change in the electrical conductivity at the boundary with listvenite, the curve 2 showing the change in the electrical conductivity within the body of the binder at a point remote from the boundaries with listvenite and sandstone, and the curve 3 showing the change in the electrical conductivity at the boundary with sandstone. Similarly to the above curves, time $\tau$ in minutes is plotted on the abscissae and the electrical conductivity $\mathscr{X}_o$ in Ohm$^{-1}$ cm$^{-1}$ is plotted on the ordinates.

Correlation between the value of the difference in the electrical conductivity and the value of adhesion is obtained by way of experiments and should be found individually for each type of binder, whereafter tables or charts for the determination of the adhesion for a given type of binder may be prepared.

Figure 3:
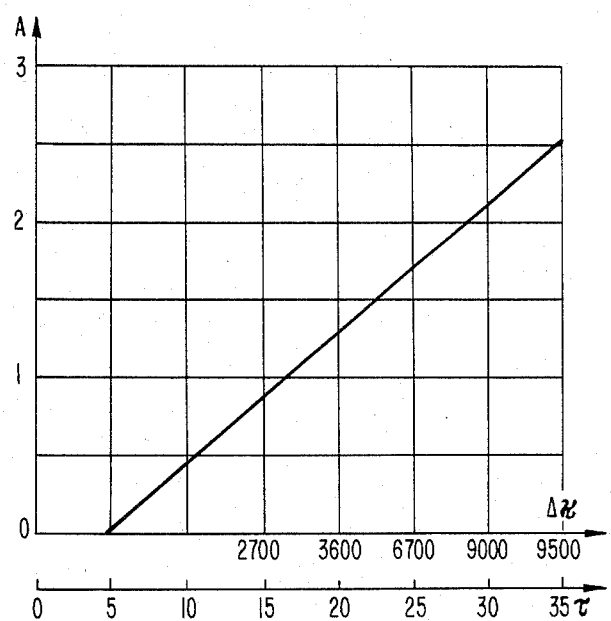
FIG. 3 shows the relationship of the value of difference in electrical conductivity within the body of the stone and at the boundary with a solid body v. adhesion to the solid body.

An example of such chart is given in FIG. 3. The product of the difference in the electrical conductivity by the time of the process since the moment of mixing $\Delta\mathscr{X}\tau 10^{-3}$ Ohm$^{-1}$ cm$^{-1}$s and the time in minutes are plotted on the abscissae. The value of adhesion A in g/cm$^2$ is plotted on the ordinates.

An apparatus for measuring kinetics of structure formation of binders comprises an a-c voltage generator 1 (FIG. 4), a pick-up 2 for measuring the electrical conductivity installed in the body of a product 3 of a binder and connected to the generator 1 and to a device 4 for recording the response of the product to the action by the generator 1.

The pick-up 2 for measuring the electrical conductivity is connected to the device 4 via a series circuit including a differential inductive bridge circuit 5, a voltage amplifier 6, and a phase detector 7. The other output of the generator 1 is connected to the input of the phase detector 7.

The differential inductive bridge circuit 5 converts changes in the electrical conductivity into a signal of an a-c voltage which is proportional to the value of total electrical conductivity. The a-c voltage amplifier 6 amplifies this signal to a value suitable for recording, and the phase detector 7 converts the a-c voltage proportional to the electrical conductivity into a d-c voltage proportional to the active component of the electrical conductivity.

The pick-up for measuring the electrical conductivity comprises a pair of electrodes of an area between 0.1 and 0.3 cm$^2$ of cylindrical or plate-shaped form made of brass, stainless steel, and the like and secured at a distance of 2-3 cm from each other by means of an insulator (not shown), wires being connected to the electrodes.

Figure 4:
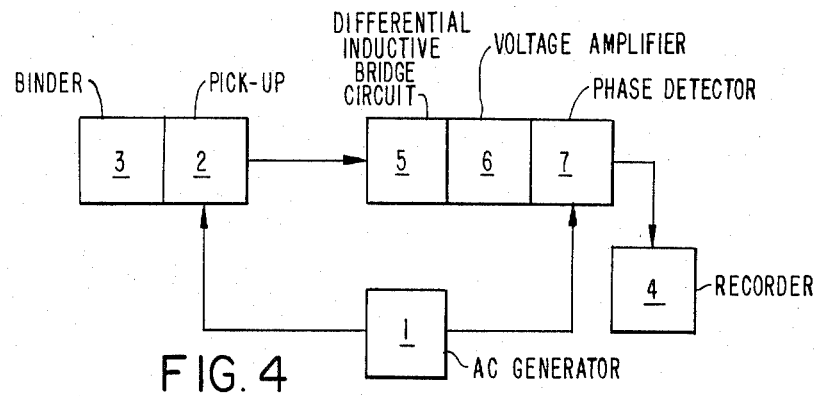
FIG. 4 is a block-diagram of an apparatus for the determination of kinetics of structure formation.
Figure 5:
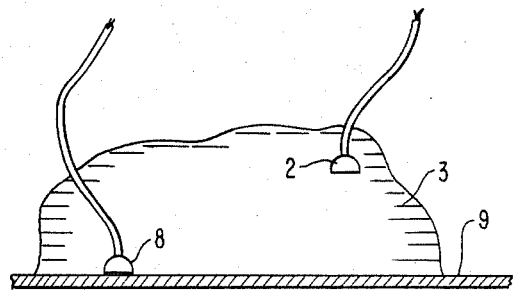
FIG. 5 shows the locations of pick-ups for measuring electrical conductivity within the volume of a product of a binder and adjacent to the zone of contact with a solid body.
Figure 6:
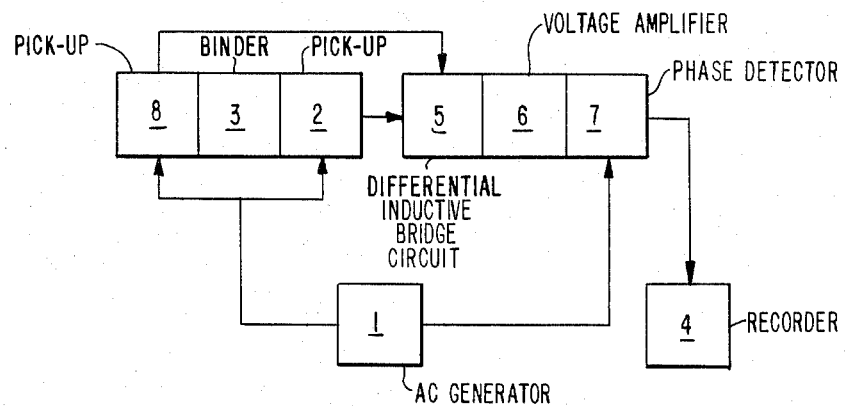
FIG. 6 is a block-diagram of an apparatus for the determination of adhesion.

An apparatus for the determination of adhesive characteristics is constructed basically along similar lines with the above-described apparatus for the determination of kinetics of structure formation. It has a second pick-up 8 for measuring the electrical conductivity (FIG. 5), which is placed in the zone of contact of the product made of a binder with a solid body 9 and connected to the differential inductive bridge circuit 5 (FIG. 6) and to the a-c voltage generator 1 similarly to the pick-up 2 (FIG. 4). Characteristics of the electrical conductivity in the zone of contact are recorded by the recording device 4 (FIG. 6).

Simultaneous recording of curves of the electrical conductivity for the internal volume of the product 3 of a binder (FIG. 5) and for the zone of its contact with the solid body 9 may be effected using a two-channel recording device having a switching circuit (not shown). The amplifier 6, the differential inductive bridge circuit 5, the a-c voltage generator 1, and the phase detector 7 may be of any appropriate known type suitable for employment in the apparatus according to the invention.

The apparatus according to the invention functions in the following manner.

For conducting the measurement of kinetics of structure formation and adhesive characteristics, the apparatus is assembled and connected to the pick-up 2 in case the kinetics is studied or to the two pick-ups 2 and 8 in case the adhesion is tested, which is made by means of a standard two-channel recorder having a switching circuit. Before mixing the binder, the apparatus is prepared for operation by connecting it to a source of supply voltage. Then the recording device 4 is turned on and, after the preparation of a sample of the product 3 made of a binder, the pick-up 2 for measuring the electrical conductivity is immersed in the body of the sample and, in case the adhesive characteristics are measured, the pick-up 8 for measuring the electrical conductivity is installed adjacent to the zone of contact of the product 3 made of a binder and the solid body 9 within 0.1–1 mm from the surface of the solid body 9. The pick-ups 2 and 8 should be placed rather rapidly, especially in determining the kinetics of structure formation in quick-setting so as to have the time for recording the hydration which takes place during the first stage.

An a-c signal proportional to the electrical conductivity of the product 3 made of the binder flows through the circuit consisting of the a-c voltage generator 1, the pick-up 2 of the pick-ups 2 and 8 enabling the flow of the current through the sample 3 of the binder, and the differential inductive bridge circuit 5 in which the current signal is converted into an a-c voltage signal proportional to the electrical conductivity. This signal is amplified by the amplifier 6 to a value suitable for the recording and detected by the phase detector 7 which samples the active component of the signal and converts it into a d-c voltage adapted for feeding to the recording device 4. The process is recorded until the flatening of the curve, and the apparatus is then turned off.

What we claim:

1. A process for monitoring structural changes in a binder having at least one solid object in contact therewith, during curing of the binder, comprising the steps of:
   immersing a first conductivity monitoring pickup in a zone of said binder at the boundary between the binder and said solid object;
   immersing a second conductivity monitoring pickup in a zone of said binder remote from said boundary;
   applying an AC voltage not exeeding 50 mv. to each of said pickups, said voltage having a frequency in the range of about 5 KHz. to about 30 KHz., to cause each pickup to provide an output signal corresponding to the electrical conductivity of the corresponding binder zone;
   comparing said output signals to provide a differential output signal corresponding to the difference in electrical conductivity of the binder between said zones and indicative of the extent of adhesion of said binder to said solid object; and
   displaying or recording said differential output signal.

2. The process according to claim 1, wherein said comparing step comprises comparing only those components of said pick-up output signals which are in phase with said AC voltage.

* * * * *